(12) United States Patent
Kim et al.

(10) Patent No.: US 10,925,699 B2
(45) Date of Patent: Feb. 23, 2021

(54) IMAGE GENERATION SYSTEM FOR IMPLANT DIAGNOSIS AND GENERATION METHOD THEREOF

(71) Applicants: MEGAGEN IMPLANT CO., LTD., Gyeongsan-si (KR); Jong Cheol Kim, Daegu (KR)

(72) Inventors: Jong Cheol Kim, Daegu (KR); Kwang Bum Park, Daegu (KR)

(73) Assignees: MEGAGEN IMPLANT CO., LTD.; Jong Cheol Kim

( * ) Notice: Subject to any disclaimer, the term of this patent is extended or adjusted under 35 U.S.C. 154(b) by 0 days.

(21) Appl. No.: 16/340,099

(22) PCT Filed: Jan. 10, 2017

(86) PCT No.: PCT/KR2017/000321
§ 371 (c)(1),
(2) Date: Apr. 5, 2019

(87) PCT Pub. No.: WO2018/066763
PCT Pub. Date: Apr. 12, 2018

(65) Prior Publication Data
US 2020/0046474 A1    Feb. 13, 2020

(30) Foreign Application Priority Data
Oct. 6, 2016 (KR) .................. 10-2016-0129287

(51) Int. Cl.
*A61C 13/34* (2006.01)
*G06T 7/33* (2017.01)
(Continued)

(52) U.S. Cl.
CPC ............ *A61C 13/34* (2013.01); *A61C 9/0046* (2013.01); *G06T 7/337* (2017.01); *G06T 19/20* (2013.01);
(Continued)

(58) Field of Classification Search
None
See application file for complete search history.

(56) References Cited

U.S. PATENT DOCUMENTS 8,798,346 B2    8/2014 Cizek
2011/0008751 A1*    1/2011 Pettersson .......... A61C 13/0004
433/167
(Continued)

FOREIGN PATENT DOCUMENTS

KR    20140111902 A    9/2014
KR    101544773 B1    8/2015
(Continued)

OTHER PUBLICATIONS

Extended European Search Report for Application No. 17858558.4 dated Sep. 26, 2019.

*Primary Examiner* — Yingchun He
(74) *Attorney, Agent, or Firm* — Renaissance IP Law Group LLP

(57) ABSTRACT

An image generation system for implant diagnosis includes a first image information acquirement apparatus acquiring first three-dimensional (3D) image data about a mouth area of a target patient, a second image information acquirement apparatus acquiring second 3D image data by scanning plaster patterns of teeth of the target patient, and a data processing apparatus receiving and matching the first 3D image data and the second 3D image data and generating synthetic 3D image data. In the image generation system, the plaster patterns of teeth are provided with a matching reference marker for matching the first 3D image data and the second 3D image data, and the data processing apparatus pre-matches the first 3D image data and the second 3D image data based on a coordinate of a matching reference marker of the second 3D image data.

8 Claims, 9 Drawing Sheets

(51) Int. Cl.
*A61C 9/00* (2006.01)
*G06T 19/20* (2011.01)
*A61B 6/00* (2006.01)
*A61C 13/00* (2006.01)

(52) U.S. Cl.
CPC .................. *G06T 2200/24* (2013.01); *G06T 2207/10081* (2013.01); *G06T 2207/20101* (2013.01); *G06T 2207/30036* (2013.01); *G06T 2207/30052* (2013.01); *G06T 2207/30204* (2013.01); *G06T 2219/008* (2013.01); *G06T 2219/028* (2013.01); *G06T 2219/2004* (2013.01)

(56) References Cited

U.S. PATENT DOCUMENTS

2011/0050848 A1* 3/2011 Rohaly .................. G06T 15/10
 348/43
2015/0091778 A1 4/2015 Day et al.
2015/0265372 A1* 9/2015 Kim .......................... G06T 7/13
 433/75

FOREIGN PATENT DOCUMENTS

| KR | 101554157 B1 | 9/2015 |
| KR | 20160002703 A | 1/2016 |
| WO | 2008083857 A1 | 7/2008 |

* cited by examiner

IMAGE GENERATION SYSTEM FOR IMPLANT DIAGNOSIS AND GENERATION METHOD THEREOF

TECHNICAL FIELD

The inventive concept relates to an image generation system for implant diagnosis and a generation method thereof, and more particularly, to an image generation system for implant diagnosis which is used for diagnosis and surgery planning of a dental implant, and a generation method thereof.

BACKGROUND ART

An implant originally means a substitute used to restore lost human tissues. In a dental field, however, the implant refers to a series of procedures to transplant an artificial tooth.

To replace a lost dental root, the implant is a series of dental procedures to restore the function of a tooth by placing a fixture, which is a dental root formed of titanium and having no rejection to a human body, in an alveolar bone where a tooth is lost, and then fixing an artificial tooth thereto.

In the case of a general prosthesis or denture, surrounding teeth or bones may be damaged as time passes. In contrast, since the implant does not harm the surrounding tooth tissues, provides the same function and shape as a natural tooth, and has no tooth decay, the implant may be used semi-permanently.

In an artificial tooth surgery (referred to as an implant or an implant surgery), a implantation hole is formed by using a drill, which varies according to the type of a fixture, the fixture is placed in the alveolar bone and has osseointegration with the bone, and an abutment is coupled to the fixture and crowned with a final prosthesis.

The implant as above may facilitate restoration of a single missing tooth, enhance the function of a denture for partially toothless and fully toothless patients, improve an aesthetic aspect of dental prosthesis restoration, and furthermore distribute excessive stress applied to surrounding support bone tissues and stabilize a row of teeth.

In order to increase accuracy of an implant surgery in an implant surgery process, a simulation surgery and surgery planning are accompanied. In the simulation surgery and surgery planning, accurate data about a mouth area of a target patient is essential.

In general, to obtain data about a mouth area of a target patient, an image of the mouth area of a target patient is captured by using a computed tomography (CT) apparatus, thereby obtaining data of a three-dimensional image.

However, while the CT data obtained by the CT apparatus has a merit of enabling accurate identification of a bone shape of the target patient, it may be difficult to accurately identify the shape of gum and an image may be distorted by variously shaped prostheses and implants provided in a mouth of a target patient.

Accordingly, hybrid data is used for simulation surgery. The hybrid data is obtained by scanning, by using a 3D scanner, plaster patterns of teeth manufactured in an internal mouth shape of the target patient obtained by using an impression material, to obtain scan data, and then overlapping CT data and the scan data and replacing the CT data about an internal area of a mouth of the target patient with the scan data.

In order to generate the hybrid data by overlapping the CT data and the scan data, a operation of matching the CT data and the scan data is needed. Korea Patent Registration No. 10-1315032 discloses a method of matching CT data obtained when a bite having a reference plate is inserted in the mouth of a target patient and scan data obtained by scanning plaster patterns of teeth obtained when the bite is inserted into the mouth of a target patient, with respect to the reference plate.

However, the conventional method of matching data with respect to the bite having a reference plate has problems, for example, the bite having a reference plate CT frequently hides the mouth area of a target patient during image capturing and an image of the CT data is distorted as the bite interferes with the CT data. Thus, since a process of removing a bite portion from the obtained CT data and scan data is necessary, lots of time is spent in the data matching operation.

DISCLOSURE

Technical Problem

The inventive concept provides an image generation system for implant diagnosis which may fast match three-dimensional (3D) image data obtained by capturing an image of a mouth area of a target patient and 3D image data obtained by scanning plaster patterns of teeth of the target patient, and a generation method thereof.

Technical Solution

According to an aspect of the inventive concept, there is provided an image generation system for implant diagnosis, which includes a first image information acquirement apparatus acquiring first three-dimensional (3D) image data about a mouth area of a target patient, a second image information acquirement apparatus acquiring second 3D image data by scanning plaster patterns of teeth of the target patient, and a data processing apparatus receiving and matching the first 3D image data and the second 3D image data and generating synthetic 3D image data, in which the plaster patterns of teeth are provided with a matching reference marker for matching the first 3D image data and the second 3D image data, and the data processing apparatus pre-matches the first 3D image data and the second 3D image data based on a coordinate of a matching reference marker of the second 3D image data.

The matching reference marker may be provided plurally, and the plurality of matching reference markers may be arranged spaced apart from one another.

The data processing apparatus may include an input unit receiving information from a user, an operation unit generating the synthetic 3D image data, electrically connected to the input unit, and correcting the synthetic 3D image data based on the information input from the user, and a display unit electrically connected to the operation unit and visually displaying the synthetic 3D image data.

The data processing apparatus may generate the synthetic 3D image data by performing a pre-matching operation of pre-matching the first 3D image data and the second 3D image data based on the coordinate of the matching reference marker of the second 3D image data and then performing a precise matching operation of precisely matching the second 3D image data to the first 3D image data in the pre-matched synthetic 3D image data.

In the pre-matching operation, the operation unit may section a display area of the display unit into a teeth area display zone in which a teeth area of the target patient of the first 3D image data is visually displayed, a second 3D image data display zone in which the second 3D image data is visually displayed, and a synthetic 3D image data display zone in which the synthetic 3D image data is visually displayed, receive an input of the coordinate of the matching reference marker in the second 3D image data display zone through the input unit, receive an input of a virtual coordinate corresponding to the coordinate of the matching reference marker in the teeth area display zone through the input unit, and display the pre-matched synthetic 3D image data in the synthetic 3D image data display zone by matching the input coordinate of the matching reference marker G2 and the input virtual coordinate.

In the precise matching operation, the operation unit may section the display area of the display unit into a plurality of divided zones, arrange different plane images of the pre-matched synthetic 3D image data in the plurality of divided zones, and receive an input of a state of matching the second 3D image data to the first 3D image data in each divided zone through the input unit.

The plurality of divided zones may include a first area in which a plane image obtained by cutting the pre-matched synthetic 3D image data along a first axis and a second axis crossing the first axis is displayed, a second area in which a plane image obtained by cutting the pre-matched synthetic 3D image data along the second axis and a third axis crossing the second axis at a position of a first movement point displayed in the first area is displayed, a third area in which a plane image obtained by cutting the pre-matched synthetic 3D image data along the first axis and the third axis at the position of the first movement point displayed in the first area is displayed, a fourth area in which a plane image obtained by cutting the pre-matched synthetic 3D image data along the second axis and the third axis at a position of a second movement point displayed in the first area is displayed, a fifth area in which a plane image obtained by cutting the pre-matched synthetic 3D image data along the first axis and the third axis at the position of the second movement point displayed in the first area is displayed, and a sixth area in which a plane image obtained by cutting the pre-matched synthetic 3D image data along the second axis and the third axis at a position of a third movement point displayed in the first area is displayed.

The first to third movement points may be movable by an operation of the user, the images of the second area and the third area may be changed linked with a movement of the first movement point, the images of the fourth area and the fifth area may be changed linked with a movement of the second movement point, and the image of the sixth area may be changed linked with a movement of the third movement point.

According to another aspect of the inventive concept, there is provided a method of generating an image for implant diagnosis, which includes a first image information acquirement operation of acquiring first 3D image data about a mouth area of a target patient, a second image information acquirement operation of acquiring second 3D image data by scanning plaster patterns of teeth of the target patient, and a synthetic 3D image data acquirement operation of generating synthetic 3D image data by matching the first 3D image data and the second 3D image data, in which the second image information acquirement operation comprises providing a matching reference marker for matching the first 3D image data and the second 3D image data on the plaster patterns of teeth of the target patient, and the synthetic 3D image data acquirement operation comprises a pre-matching operation of pre-matching the first 3D image data to the second 3D image data based on a coordinate of the matching reference marker of the second 3D image data.

The pre-matching operation may include sectioning a display area of the display unit into a teeth area display zone in which a teeth area of the target patient of the first 3D image data is visually displayed, a second 3D image data display zone in which the second 3D image data is visually displayed, and a synthetic 3D image data display zone in which the synthetic 3D image data is visually displayed, receiving an input of the coordinate of the matching reference marker in the second 3D image data display zone, receiving an input of a virtual coordinate corresponding to the coordinate of the matching reference marker in the teeth area display zone, and displaying the pre-matched synthetic 3D image data in the synthetic 3D image data display zone by matching the input coordinate of the matching reference marker G2 and the input virtual coordinate.

The matching reference marker may be provided plurally, and the plurality of matching reference markers may be arranged spaced apart from one another.

The synthetic 3D image data acquirement operation may further include a precise matching operation of precisely matching the second 3D image data to the first 3D image data in the pre-matched synthetic 3D image data.

The precise matching operation may include sectioning the display area of the display unit into a plurality of divided zones and arranging different plane images of the pre-matched synthetic 3D image data in the plurality of divided zones, and performing correction such that the second 3D image data is matched to the first 3D image data in each divided area.

The plurality of divided zones may include a first area in which a plane image obtained by cutting the pre-matched synthetic 3D image data along a first axis and a second axis crossing the first axis is displayed, a second area in which a plane image obtained by cutting the pre-matched synthetic 3D image data along the second axis and a third axis crossing the second axis at a position of a first movement point displayed in the first area is displayed, a third area in which a plane image obtained by cutting the pre-matched synthetic 3D image data along the first axis and the third axis at the position of the first movement point displayed in the first area is displayed, a fourth area in which a plane image obtained by cutting the pre-matched synthetic 3D image data along the second axis and the third axis at a position of a second movement point displayed in the first area is displayed, a fifth area in which a plane image obtained by cutting the pre-matched synthetic 3D image data along the first axis and the third axis at the position of the second movement point displayed in the first area is displayed, and a sixth area in which a plane image obtained by cutting the pre-matched synthetic 3D image data along the second axis and the third axis at a position of a third movement point displayed in the first area is displayed.

The first to third movement points may be movable by an operation of the user, the images of the second area and the third area may be changed linked with a movement of the first movement point, the images of the fourth area and the fifth area may be changed linked with a movement of the second movement point, and the image of the sixth area may be changed linked with a movement of the third movement point.

The second image information acquirement operation may further includes generating the plaster patterns of teeth of the target patient before the providing of the matching reference marker, and scanning the plaster patterns of teeth of the target patient after the providing of the matching reference marker.

Advantageous Effects

According to the exemplary embodiments of the present invention, since the pre-matching operation is provided in which the first 3D image data is pre-matched to the second 3D image data based on the coordinate of the matching reference marker of the second 3D image data, the first 3D image data and the second 3D image data may be fast matched to each other.

According to the exemplary embodiments of the present invention, since the data processing apparatus is provided in which the first 3D image data data is pre-matched to the second 3D image data based on the coordinate of the matching reference marker of the second 3D image data, the first 3D image data and the second 3D image data may be fast matched to each other.

Furthermore, according to the exemplary embodiments of the present invention, since the pre-matching operation is provided in which the first 3D image data is pre-matched to the second 3D image data based on the coordinate of the matching reference marker of the second 3D image data, the first 3D image data and the second 3D image data may be fast matched to each other.

MODES OF THE INVENTION

Figure 1:
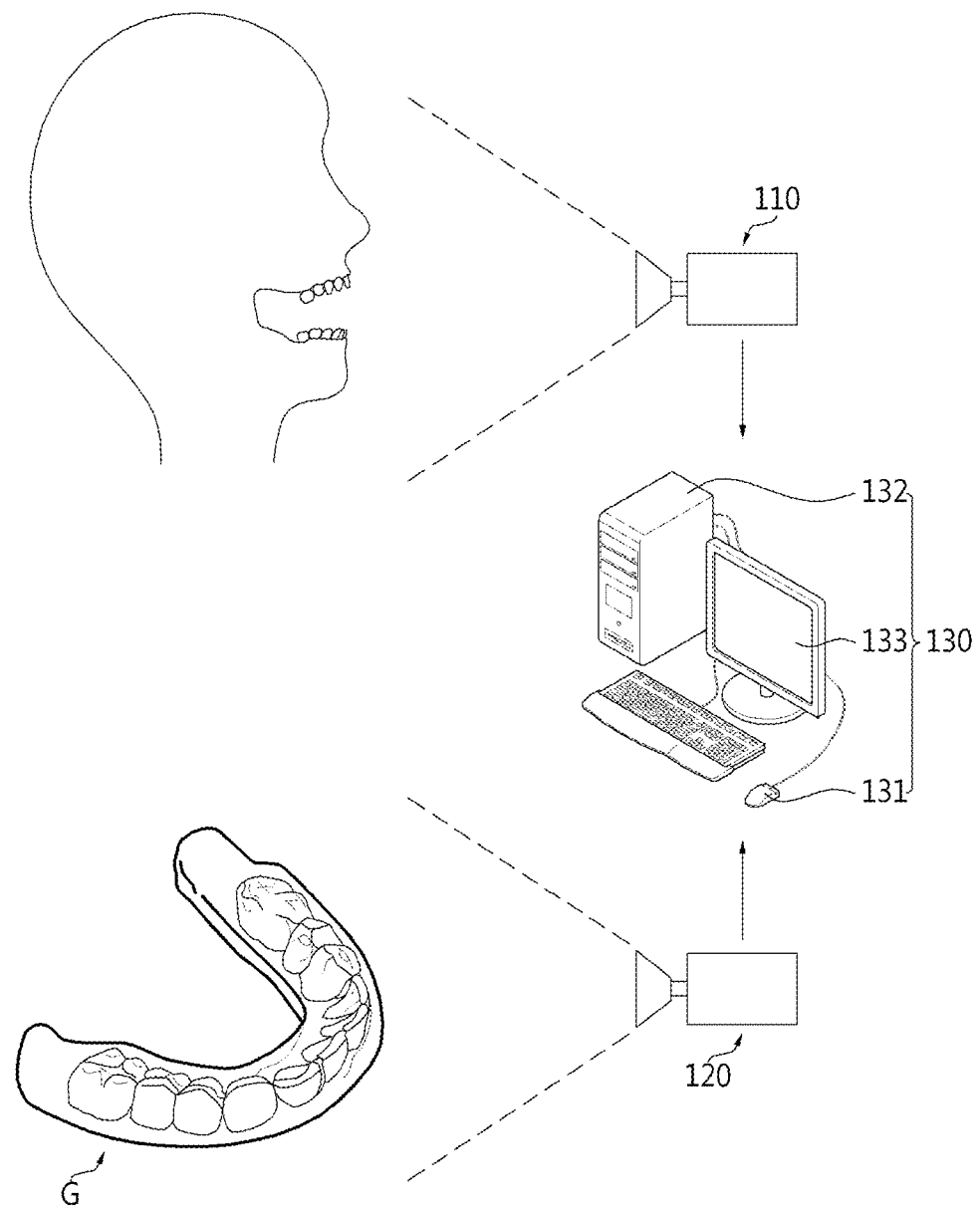
FIG. 1 illustrates an image generation system for implant diagnosis according to an embodiment.

The attached drawings for illustrating exemplary embodiments of the inventive concept are referred to in order to gain a sufficient understanding of the inventive concept and the merits thereof.

Hereinafter, the inventive concept will be described in detail by explaining exemplary embodiments of the inventive concept with reference to the attached drawings. Like reference numerals in the drawings denote like elements.

In the following description, a first axis, a second axis, and a third axis denote an X-axis, a Y-axis, and a Z-axis, respectively.

Figure 2:
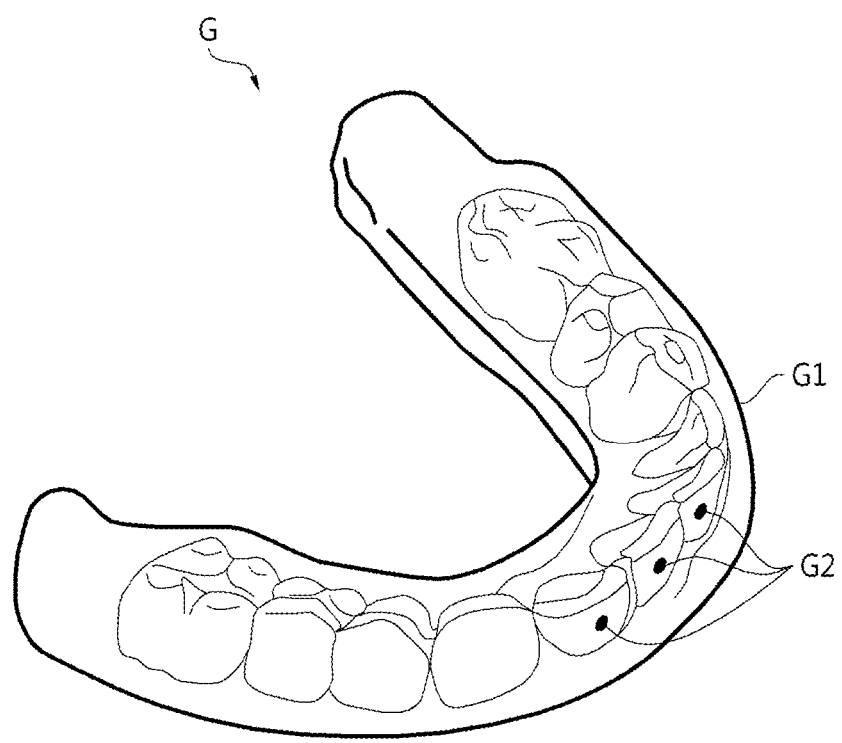
FIG. 2 illustrates the plaster patterns of teeth of FIG. 1.
Figure 3:
FIGS. 3 and 4 are images visually displaying bone density around a virtual fixture on a display unit of FIG. 1.
Figure 4:

FIG. 1 illustrates an image generation system for implant diagnosis according to an embodiment. FIG. 2 illustrates the plaster patterns of teeth of FIG. 1. FIGS. 3 and 4 are images visually displaying bone density around a virtual fixture on a display unit of FIG. 1.

The image generation system for implant diagnosis according to the present embodiment, as illustrated in FIGS. 1 to 4, may include a first image information acquirement apparatus 110 for obtaining first three-dimensional (3D) image data about a mouth area of a target patient, a second image information acquirement apparatus 120 for obtaining second 3D image data by scanning plaster patterns of teeth G of the target patient, and a data processing apparatus 130 for receiving and matching the first 3D image data and the second 3D image data to generate synthetic 3D image data.

The first image information acquirement apparatus 110 acquires the first 3D image data about the mouth area of the target patient. The first image information acquirement apparatus 110 of the present embodiment may include computed tomography (CT) and the first 3D image data of the present embodiment signifies a 3D image implemented by using a plurality of sectional images, but the present inventive concept is not limited thereto and a variety of imaging apparatuses such as an magnetic resonance imaging apparatus may be used as the first image information acquirement apparatus 110 of the present embodiment.

The second image information acquirement apparatus 120 acquires second 3D image data by scanning the plaster patterns of teeth G of the target patient.

The plaster patterns of teeth G of the present embodiment are formed in a shape of teeth and gum of the target patient. After a tray with an impression material is inserted in the mouth of the target patient, the teeth of the target patient press the impression material and thus the plaster patterns of teeth G are manufactured in a shape of impressed teeth and surrounding gum.

The plaster patterns of teeth G of the present embodiment are provided with a matching reference marker G2 for matching the first 3D image data and the second 3D image data.

The matching reference marker G2 is used as a reference coordinate for the matching of the first 3D image data and the second 3D image data. The matching reference marker G2 may be used when the data processing apparatus 130 generates synthetic 3D image data by matching a coordinate of the matching reference marker G2 of the second 3D image data and a coordinate of a virtual position corresponding to the matching reference marker G2 in the first 3D image data.

The matching reference marker G2 of the present embodiment is provided plurally and the plurality of matching reference markers G2 are arranged spaced apart from one another. In the present embodiment, at least three matching reference markers G2 are provided and the at least three matching reference markers G2 are arranged spaced apart from one another.

The matching reference marker G2 is formed in a structure or material to be distinguished from plaster patterns of teeth main body G1 in the second 3D image data.

The second image information acquirement apparatus 120 may include a 3D scanner (not shown) that acquires the second 3D image data by scanning the plaster patterns of teeth G. The second 3D image data of the present embodiment may include stereolithography (STL) data. The STL data may be in an ASCII or binary format and represents a surface of a 3D structure by a plurality of polygons in a 3D program so that modeling data of the 3D structure is easily recognized by a different type of a 3D program.

The data processing apparatus 130 receives and matches the first 3D image data and the second 3D image data, thereby generating the synthetic 3D image data.

The data processing apparatus 130 may include an input unit 131 for receiving an input of information from a user, an operation unit 132 for receiving the first 3D image data and the second 3D image data and generating the synthetic 3D image data, and a display unit 133 electrically connected to the operation unit 132 and visually displaying the synthetic 3D image data.

The input unit 131 is electrically connected to the operation unit 132, and receives an input of control information from the user and transmits the received information to the operation unit 132.

The operation unit 132 receives the first 3D image data and the second 3D image data, generates the synthetic 3D image data, and visually displays the generated data on the display unit 133.

In other words, the synthetic 3D image data is generated through the organic interaction among the input unit 131, the display unit 133, and the operation unit 132.

The generation of the synthetic 3D image data is briefly described now, and will be described in detail later.

The first 3D image data acquired from the first image information acquirement apparatus 110 such as a CT apparatus has a merit of enabling the accurate identification of a bone shape of a target patient. However, an image may be distorted by variously shaped prostheses and implants provided in the mouth of the target patient.

Accordingly, the synthetic 3D image data is generated, in which the second 3D image data containing very accurate information about the internal structure of the mouth of the target patient, which is acquired by scanning the plaster patterns of teeth G of the target patient, and the first 3D image data containing accurate information about the bone shape of the target patient are overlapped. An operation of matching the first 3D image data and the second 3D image data is needed to overlap the first 3D image data and the second 3D image data.

The operation of matching the first 3D image data and the second 3D image data may include a pre-matching operation of pre-matching the first 3D image data and the second 3D image data based on the coordinate of the matching reference marker G2 of the second 3D image data, and a precise matching operation of precisely matching the second 3D image data with the first 3D image data in the pre-matched synthetic 3D image data.

The pre-matching operation is a method of substantially fast matching the first 3D image data and the second 3D image data. In the pre-matching operation, the first 3D image data and the second 3D image data are pre-matched based on the coordinate of the matching reference marker G2 of the second 3D image data.

Figure 6:
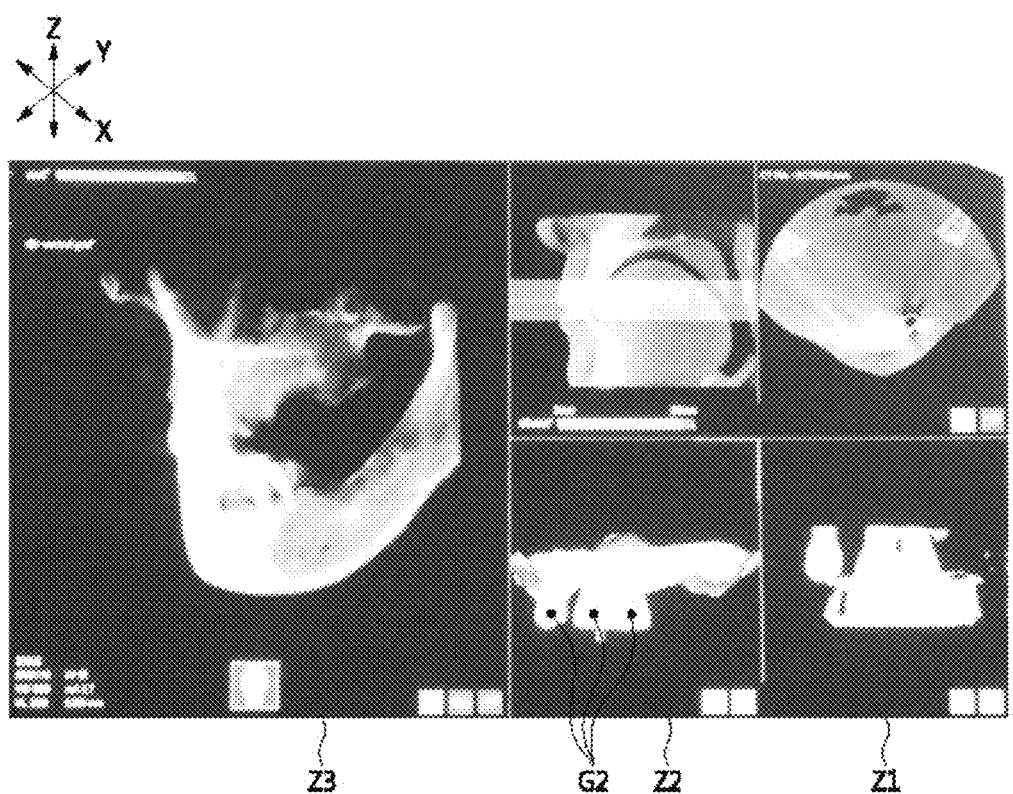
FIGS. 6 and 7 are images of the display unit in a pre-matching operation of the synthetic 3D image data acquirement operation of FIG. 5.
Figure 7:
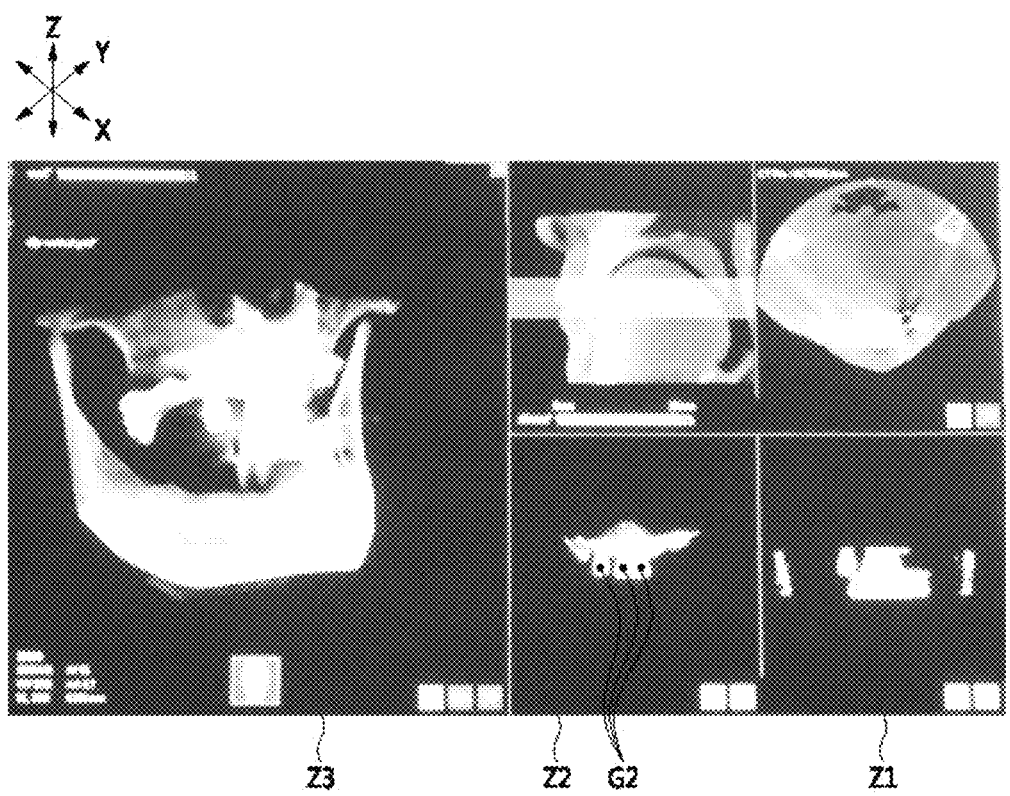

In the pre-matching operation, the user is provided with a screen as illustrated in FIGS. 6 and 7 through the screen of the display unit 133. The screen may include a teeth area display zone Z1 in which a teeth area of the target patient of the first 3D image data is visually displayed, a second 3D image data display zone Z2 in which the second 3D image data is visually displayed, and a synthetic 3D image data display zone Z3 in which the synthetic 3D image data is visually displayed.

The teeth area of the target patient of the first 3D image data is visually displayed in the teeth area display zone Z1. The teeth area of the target patient of the first 3D image data that is visually displayed in the teeth area display zone Z1 may be selected by a control signal through the input unit 131 by the user.

Furthermore, the second 3D image data is visually displayed in the second 3D image data display zone Z2. The synthetic 3D image data is visually displayed in the synthetic 3D image data display zone Z3.

In a screen of the display unit 133 of FIG. 6, the user inputs to the operation unit 132 the coordinate of the matching reference marker G2 in the second 3D image data display zone Z2. In other words, when the user clicks three matching reference markers G2 displayed in the second 3D image data display zone Z2 through the input unit 131 such as a mouse or the like, a clicked coordinate is transmitted to the operation unit 132.

Then, the user inputs a virtual coordinate corresponding to the coordinate of the matching reference marker G2 in the teeth area display zone Z1 to the operation unit 132. In other words, when the user compares an image of a teeth area displayed in the teeth area display zone Z1 and an image of the plaster patterns of teeth G displayed in the second 3D image data display zone Z2 and clicks a virtual position corresponding to the matching reference marker G2 in an image of the teeth area displayed in the teeth area display zone Z1, the clicked coordinate is transmitted to the operation unit 132.

Then, the operation unit 132 compares the input coordinate of the matching reference marker G2 and the input virtual coordinate, overlaps the first 3D image data and the second 3D image data, and displays in the synthetic 3D image data display zone Z3 pre-matched synthetic 3D image data obtained by overlapping the first 3D image data and the second 3D image data.

While the synthetic 3D image data display zone Z3 of FIG. 6 displays only the first 3D image data because the user's input of a coordinate is not performed, the synthetic 3D image data display zone Z3 of FIG. 7 displays synthetic 3D image data in which the second 3D image data is pre-matched with the first 3D image data as the coordinate of the matching reference marker G2 and the virtual coordinate corresponding to the coordinate of the matching reference marker G2 are input.

Since the pre-matching operation is performed as the user compares the image of the teeth area display zone Z1 and the image of the second 3D image data display zone Z2 and clicks a virtual position corresponding to the matching reference marker G2 in the image of the teeth area display zone Z1, although a degree of matching of the pre-matched synthetic 3D image data passing through the pre-matching operation is not in a perfect state, the pre-matched synthetic 3D image data passing through the pre-matching operation is in an almost matched state.

Accordingly, in the precise matching operation, in the pre-matched synthetic 3D image data in the almost matched state, the second 3D image data is precisely matched with the first 3D image data.

Figure 8:
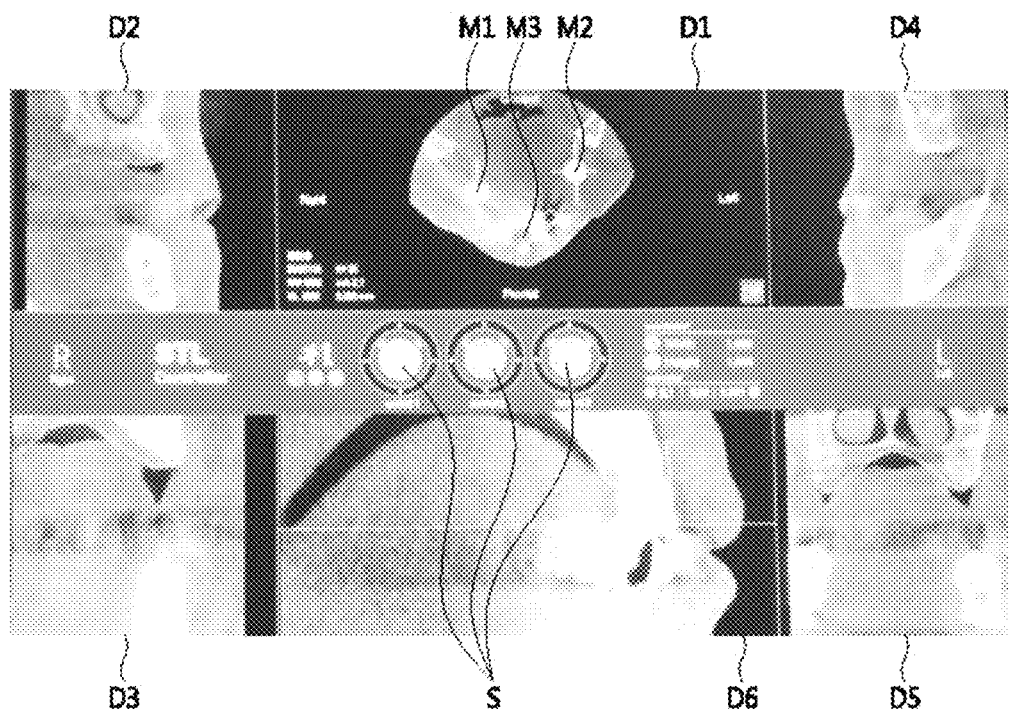
FIGS. 8 and 9 are images of the display unit in a precise matching operation of the synthetic 3D image data acquirement operation of FIG. 5.
Figure 9:
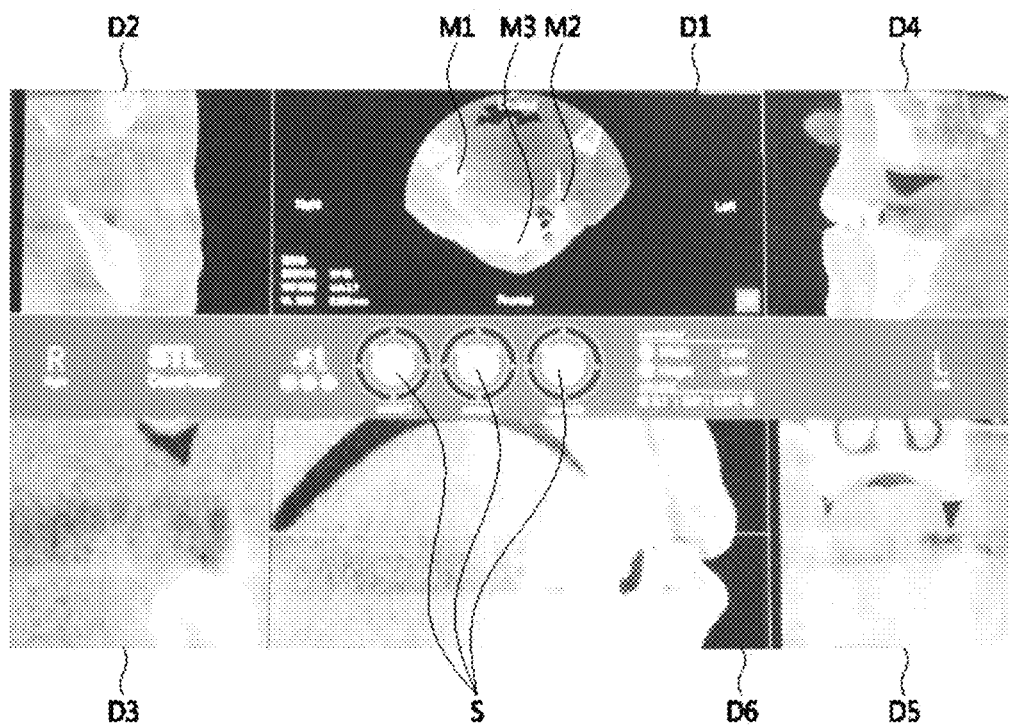

In the precise matching operation, a screen as illustrated in FIGS. 8 to 9 is provided to the user on the screen of the display unit 133. In other words, a plurality of divided zones D1, D2, D3, D4, D5, and D6 are displayed on the screen provided to the user through the display unit 133 in the precise matching operation. Different plane images of the pre-matched synthetic 3D image data are arranged in the divided areas D1, D2, D3, D4, D5, and D6.

In this state, the plane images of the pre-matched synthetic 3D image data displayed in the divided areas D1, D2, D3, D4, D5, and D6 may be distinguished by the first 3D image data and the second 3D image data (for example, outlines of the first 3D image data and the second 3D image data are displayed in different colors) so that the user may visually recognize whether the data is matched or not.

As illustrated in FIG. 8 or 9, in the precise matching operation of the present embodiment, a display area of the screen provided to the user through the display unit 133 is sectioned into the first to sixth divided areas D1, D2, D3, D4, D5, and D6.

The first divided area D1 is a plane of the pre-matched synthetic 3D image data and corresponds to a user's operation screen. In the present embodiment, the first divided area D1 displays an image of the pre-matched synthetic 3D image data cut by a plane of X-Y axes.

Three movement points M1, M2, and M3 are displayed in the first divided area D1. When the user moves an input point through the input unit 131 such as a mouse or the like, images of the second to sixth divided areas D2, D3, D4, D5, and D6 are changed.

The second divided area D2 displays an image cut by a plane of Y-Z axes at the position of the first movement point M1 of the first divided area D1. The third divided area D3 displays an image cut by a plane of the X-Z axes at the position of the first movement point M1 of the first divided area D1.

The images of the second divided area D2 and the third divided area D3 are changed to plane images at the position of the first movement point M1 moved along the movement of the first movement point M1 of the first divided area D1.

The fourth divided area D4 displays an image cut by the plane of the Y-Z axes at the second movement point M2 of the first divided area D1. The fifth divided area D5 displays an image cut by the plane of the X-Z axes at the position of the second movement point M2 of the first divided area D1.

The images of the fourth divided area D4 and the fifth divided area D5 are changed to plane images at the position of the second movement point M2 moved along the movement of the second movement point M2 of the first divided area D1.

The sixth divided area D6 displays an image cut by the plane of the Y-Z axes at the position of the third movement point M3 of the first divided area D1. The image of the sixth divided area D6 is changed to a plane image at the position of the third movement point M3 moved along the movement of the third movement point M3 of the first divided area D1.

In comparison of FIG. 8 and FIG. 9, it may be seen that the images of the second to sixth divided areas D2, D3, D4, D5, and D6 are changed according to the change in the positions of the first to third movement points M1, M2, and M3.

The images of the second to sixth divided areas D2, D3, D4, D5, and D6 are affected by the user's operation through the input unit 131. In other words, the images of the position and pose of the second 3D image data displayed in the second to sixth divided areas D2, D3, D4, D5, and D6 may be changed by the user's operation.

Accordingly, while moving the first to third movement points M1, M2, and M3, the user checks whether the first 3D image data and the second 3D image data are matched with each other at many positions in the plane image of the pre-matched synthetic 3D image data. Then, the user moves the second 3D image data relative to the first 3D image data through the input unit 131 to precisely match the first 3D image data and the second 3D image data.

As described above, since the outlines of the plane images displayed in the first to sixth divided areas D1, D2, D3, D4, D5, and D6 are expressed in different colors so that the first 3D image data and the second 3D image data may be distinguished, the user may precisely match the first 3D image data and the second 3D image data by clicking the second 3D image data through the input unit 131 such as a mouse and then dragging the clicked data.

The information about a precise matching state in which the user precisely matches an image of the second 3D image data to an image of the first 3D image data by using the input unit 131 is input to the operation unit 132. The operation unit 132 generates precisely matched synthetic 3D image data by correcting the pre-matched synthetic 3D image data according to the information about a precise matching state input by the input unit 131.

After generating the precisely matched synthetic 3D image data, the operation unit 132 overlaps the second 3D image data on the first 3D image data and replaces a portion of the first 3D image data, which corresponds to the second 3D image data, with the second 3D image data, thereby generating final synthetic 3D image data.

When the generation of the above synthetic 3D image data is completed, a position of a fixture P to be placed to the target patient is determined from the synthetic 3D image data. In this state, the user determines the position of the fixture P by overlapping the virtual fixture P to be placed to the target patient on various positions of the synthetic 3D image data displayed on the display unit 133.

When the virtual fixture P to be placed to the target patient overlaps the synthetic 3D image data, the data processing apparatus 130 of the present embodiment visually displays bone density around the virtual fixture P with respect to the virtual fixture P.

In other words, in the present embodiment, when the virtual fixture P to be placed to the target patient overlaps the synthetic 3D image data, the operation unit 132 calculates bone density around the virtual fixture P with respect to the virtual fixture P.

In the present embodiment, the bone density around the virtual fixture P refers to the bone density of an area in contact with the outer contour of the virtual fixture P, that is, the bone density of a portion of the fixture P where the outline of a thread of the fixture P is located.

The display unit 133 is electrically connected to the operation unit 132 and visually displays the synthetic 3D image data, for example, in a 2D plane image and a 3D image. The display unit 133 may display not only the synthetic 3D image data, but also the first 3D image data and the second 3D image data, as a visual image.

Furthermore, the display unit 133 of the present embodiment visually displays the bone density around the virtual fixture P based on the virtual fixture P calculated in the operation unit 132.

In other words, the display unit 133, as illustrated in FIGS. 3 and 4, visually displays the bone density of an area in contact with the outer contour of the virtual fixture P calculated in the operation unit 132. In the present embodiment, the bone density around the virtual fixture P display on the display unit 133 may be displayed in different colors according to a value of the bone density.

Furthermore, in the present embodiment, the color display on the display unit 133 according to the value of the bone density is a chromatic color. As such, in the image generation system for implant diagnosis of the present embodiment, since the bone density around the virtual fixture P is displayed in different chromatic colors according to the value of the bone density, the user may be intuitively recognize the bone density around the virtual fixture P.

In the present embodiment, a high bone density value is displayed in yellow or green and a low bone density value is displayed in red or blue, but the present disclosure is not limited thereto and the bone density value may be displayed in various different colors.

A method of generating an image for implant diagnosis according to the image generation system for implant diagnosis of the present embodiment is described below with reference to FIGS. 1 to 9, mainly FIGS. 5 to 9.

Figure 5:
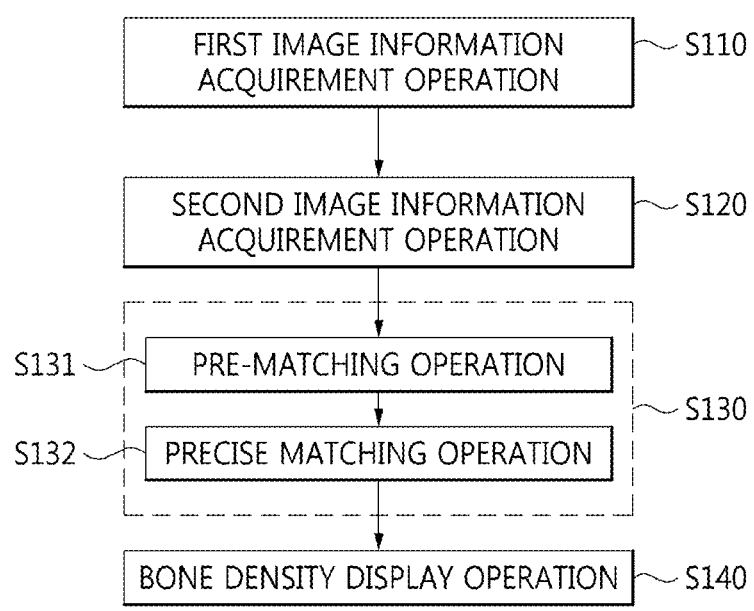
FIG. 5 is a flowchart of a method of generating an image for implant diagnosis according to the image generation system for implant diagnosis of FIG. 1.

FIG. 5 is a flowchart of a method of generating an image for implant diagnosis according to the image generation system for implant diagnosis of FIG. 1. FIGS. 6 and 7 are images of the display unit 133 in a pre-matching operation of the synthetic 3D image data acquirement operation of FIG. 5. FIGS. 8 and 9 are images of the display unit 133 in a precise matching operation of the synthetic 3D image data acquirement operation of FIG. 5.

The method of generating an image for implant diagnosis according to the present embodiment may include, as illustrated in FIG. 5, a first image information acquirement operation S110 of acquiring the first 3D image data about the mouth area of the target patient, a second image information acquirement operation S120 of acquiring the second 3D image data by scanning the plaster patterns of teeth G of the target patient, a synthetic 3D image data acquirement operation S130 of generating the synthetic 3D image data by matching the first 3D image data and the second 3D image data, and a bone density display operation S140 of visually displaying the bone density around the virtual fixture P based on the virtual fixture P when the synthetic 3D image data is overlapped with the virtual fixture P to be placed to the target patient.

In the first image information acquirement operation S110, the first 3D image data about the mouth area of the target patient is acquired. In the first image information acquirement operation S110, as illustrated in FIG. 1, the first image information acquirement apparatus 110 captures an image of the mouth area of a target patient to acquire the first 3D image data.

In the second image information acquirement operation S120, the second image information acquirement apparatus 120 scans the plaster patterns of teeth G of the target patient to acquire the second 3D image data.

In detail, the second image information acquirement operation S120 of the present embodiment may include generating the plaster patterns of teeth G of the target patient, providing the matching reference marker G2 on the plaster patterns of teeth G of the target patient, and scanning the plaster patterns of teeth G provided with the matching reference marker G2.

In the providing of the matching reference marker G2, the matching reference marker G2 for matching the second 3D image data to the plaster patterns of teeth main body G1 of the target patient manufactured in the generating of the plaster patterns of teeth G is formed.

The matching reference marker G2 provided on the plaster patterns of teeth main body G1 is used as a reference coordinate for matching the first 3D image data and the second 3D image data in the synthetic 3D image data acquirement operation S130.

In the synthetic 3D image data acquirement operation S130, the synthetic 3D image data is generated by matching the first 3D image data and the second 3D image data.

The first 3D image data acquired from the first image information acquirement apparatus 110 such as the CT apparatus, compared to its merit of enabling the accurate identification of the bone shape of the target patient, may be problematic in that an image may be distorted by variously shaped prostheses and implants provided in the mouth of the target patient.

Accordingly, the synthetic 3D image data is generated in which the second 3D image data containing very accurate information about the internal structure of the mouth of the target patient, which is acquired by scanning the plaster patterns of teeth G of the target patient, and the first 3D image data containing accurate information about the bone shape of the target patient are overlapped, and the matching operation that is essentially performed for the overlapping of the first 3D image data and the second 3D image data is performed in the synthetic 3D image data acquirement operation S130.

The synthetic 3D image data acquirement operation S130 may include a pre-matching operation S131 of pre-matching the first 3D image data and the second 3D image data based on the coordinate of the matching reference marker G2 of the second 3D image data, and a precise matching operation S132 of precisely matching the second 3D image data to the first 3D image data in the pre-matched synthetic 3D image data.

The pre-matching operation S131 is a method of substantially fast matching the first 3D image data and the second 3D image data. In the pre-matching operation S131, the first 3D image data and the second 3D image data are pre-matched based on the coordinate of the matching reference marker G2 of the second 3D image data.

The pre-matching operation S131 may include sectioning a display area of the screen provided to the user into the teeth area display zone Z1 in which a teeth area of the target patient of the first 3D image data is visually displayed, the second 3D image data display zone Z2 in which the second 3D image data is visually displayed, and the synthetic 3D image data display zone Z3 in which the synthetic 3D image data is visually displayed, a reference marker coordinate input operation of inputting the coordinate of the matching reference marker G2 in the second 3D image data display zone Z2, a virtual coordinate input operation of inputting the virtual coordinate corresponding to the coordinate of the matching reference marker G2 in the teeth area display zone Z1, and displaying the pre-matched synthetic 3D image data in the synthetic 3D image data display zone Z3 by matching the input coordinate of the matching reference marker G2 and the input virtual coordinate.

The pre-matching operation S131 is described below with reference to FIGS. 6 and 7. As illustrated in FIG. 6, the display area of a screen provided to the user through the display unit 133 is sectioned into the teeth area display zone Z1 in which the teeth area of the target patient of the first 3D image data is visually displayed, the second 3D image data display zone Z2 in which the second 3D image data is visually displayed, and the synthetic 3D image data display zone Z3 in which the synthetic 3D image data is visually displayed.

In the teeth area display zone Z1, the teeth area of the target patient of the first 3D image data is visually displayed. The teeth area of the target patient displayed in the teeth area display zone Z1 may be selected according to the user's control signal input through the input unit 131.

Furthermore, the second 3D image data is visually displayed in the second 3D image data display zone Z2, and the synthetic 3D image data is visually displayed in the synthetic 3D image data display zone Z3.

Both of the teeth area of the target patient displayed in the teeth area display zone Z1 and the second 3D image data displayed in the second 3D image data display zone Z2 indicate the structure of the mouth area of a target patient. As described above, since the second 3D image data has more accurate information about the structure of the mouth area of the target patient, when the synthetic 3D image data is generated, the structure of the mouth area of the target patient of the first 3D image data is replaced with the second 3D image data. For this replacement, the first 3D image data and the second 3D image data are matched with each other through the reference marker coordinate input operation and the virtual coordinate input operation.

In the reference marker coordinate input operation, the coordinate of the matching reference marker G2 is input in the second 3D image data display zone Z2. In other words, when the user clicks three matching reference markers G2 displayed in the second 3D image data display zone Z2 by using the input unit 131 such as a mouse or the like, a clicked coordinate is transmitted to the operation unit 132.

In the virtual coordinate input operation, the virtual coordinate corresponding to the coordinate of the matching reference marker G2 is input in the teeth area display zone Z1. In other words, when the user compares an image of the teeth area displayed in the teeth area display zone Z1 and an image of the plaster patterns of teeth G displayed in the second 3D image data display zone Z2 and then clicks a virtual position corresponding to the position of the matching reference marker G2 on the image of the teeth area displayed in the teeth area display zone Z1, the clicked coordinate is transmitted to the operation unit 132.

Then, in the displaying of the pre-matched synthetic 3D image data, the coordinate of the matching reference marker G2 and the virtual coordinate input to the operation unit 132 are compared with each other to overlap the first 3D image data and the second 3D image data and thus the pre-matched synthetic 3D image data obtained by overlapping the second 3D image data to the first 3D image data is displayed in the synthetic 3D image data display zone Z3.

It may be seen that, while only the first 3D image data is displayed in the synthetic 3D image data display zone Z3 of FIG. 6 because the reference marker coordinate input operation and the virtual coordinate input operation are not performed yet, as the reference marker coordinate input operation and the virtual coordinate input operation are performed, an image of the synthetic 3D image data in which the second 3D image data is overlapped to first 3D image data is displayed in the synthetic 3D image data display zone Z3 of FIG. 7.

In the above-described virtual coordinate input operation of the pre-matching operation S131, since the user compares the image of the teeth area display zone Z1 and the image of the second 3D image data display zone Z2 and clicks a virtual position of the matching reference marker G2 on the image of the teeth area display zone Z1, although a degree of matching of the pre-matched synthetic 3D image data passing through the pre-matching operation S131 is not in a complete state, the pre-matched synthetic 3D image data passing through the pre-matching operation S131 is in an almost matched state.

Accordingly, in the precise matching operation S132, the second 3D image data is precisely matched to the first 3D image data in the pre-matched synthetic 3D image data of an almost matched state.

The precise matching operation S132 may include an operation of sectioning the display area of the screen provided to the user through the display unit 133 into a plurality of divided zones and arranging different plane images of the pre-matched synthetic 3D image data in the divided areas, and an operation of performing correction in each divided area such that the second 3D image data is matched to the first 3D image data.

As illustrated in FIG. 8 or 9, in the precise matching operation S132, the display area of the screen provided to the user through the display unit 133 is sectioned into a plurality of divided zones D1, D2, D3, D4, D5, and D6.

Different plane images of the pre-matched synthetic 3D image data are arranged in the divided areas D1, D2, D3, D4, D5, and D6.

The different plane images of the pre-matched synthetic 3D image data arranged in the divided areas D1, D2, D3, D4, D5, and D6 is distinguished by the first 3D image data and the second 3D image data (for example, the outlines of the first 3D image data and the second 3D image data are displayed in different colors) so that the user may visually recognize whether the data is matched or not.

As illustrated in FIG. 8 or 9, in the precise matching operation S132, the display area of the screen provided to the user through the display unit 133 is sectioned into the first to sixth divided areas D1, D2, D3, D4, D5, and D6.

The first divided area D1 is a plane of the pre-matched synthetic 3D image data and corresponds to a user's operation screen. In the present embodiment, the first divided area D1 displays an image of the pre-matched synthetic 3D image data cut by the plane of the X-Y axes.

Three movement points M1, M2, and M3 are displayed in the first divided area D1. When the user moves an input point through the input unit 131 such as a mouse or the like, images of the second to sixth divided areas D2, D3, D4, D5, and D6 are changed.

The second divided area D2 displays an image cut by the plane of the Y-Z axes at the position of the first movement point M1 of the first divided area D1. The third divided area D3 displays an image cut by the plane of the X-Z axes at the position of the first movement point M1 of the first divided area D1.

The images of the second divided area D2 and the third divided area D3 are changed to plane images at the position of the first movement point M1 moved along the movement of the first movement point M1 of the first divided area D1.

The fourth divided area D4 displays an image cut by the plane of the Y-Z axes at the second movement point M2 of the first divided area D1. The fifth divided area D5 displays an image cut by the plane of the X-Z axes at the position of the second movement point M2 of the first divided area D1.

The images of the fourth divided area D4 and the fifth divided area D5 are changed to plane images at the position of the second movement point M2 moved along the movement of the second movement point M2 of the first divided area D1.

The sixth divided area D6 displays an image cut by the plane of the Y-Z axes at the position of the third movement point M3 of the first divided area D1. The image of the sixth divided area D6 is changed to a plane image at the position of the third movement point M3 moved along the movement of the third movement point M3 of the first divided area D1.

In comparison of FIG. 8 and FIG. 9, it may be seen that the images of the second to sixth divided areas D2, D3, D4, D5, and D6 are changed according to the change of the positions of the first to third movement points M1, M2, and M3.

The images of the second to sixth divided areas D2, D3, D4, D5, and D6 are affected by the user's operation through the input unit 131. In other words, the images of the position and pose of the second 3D image data displayed in the second to sixth divided areas D2, D3, D4, D5, and D6 may be changed by the user's operation.

Accordingly, while moving the first to third movement points M1, M2, and M3, the user checks whether the first 3D image data and the second 3D image data are matched with each other at many positions in the plane image of the pre-matched synthetic 3D image data. Then, the user moves the second 3D image data relative to the first 3D image data through the input unit 131 to precisely match the first 3D image data and the second 3D image data.

The user may control the scale of the first 3D image data through a scale control portion S displayed in the display area of the screen provided to the user through the display unit 133. The scale of the first 3D image data is controlled to further facilitate a precise matching operation of the first 3D image data and the second 3D image data by relatively varying the overall size of the first 3D image data with respect to the second 3D image data when there is a difference in the overall size between the first 3D image data and the second 3D image data.

As such, in the method of generating an image for implant diagnosis according to the present embodiment, since the first 3D image data and the second 3D image data are substantially fast pre-matched and then the pre-matched synthetic 3D image data is substantially precisely matched again, an overall matching time may be reduced and matching accuracy may be improved.

Next, after the synthetic 3D image data acquirement operation S130 is completed by performing the precise matching operation S132, the user establishes surgery planning. During the surgery planning, the bone density of an alveolar bone of the target patient is a very important factor, and the position, depth, and direction of placement of an implant are determined according to the state of the bone density of the target patient.

Accordingly, the bone density of an area where the fixture P is placed is very important. In the bone density display operation S140 of the present embodiment, the bone density of an area where the fixture P is placed is displayed very intuitively.

In other words, in the bone density display operation S140 of the present embodiment, as illustrated in FIGS. 3 and 4, by overlapping the virtual fixture P to be placed to the target patient to synthetic 3D image data, the bone density around the virtual fixture P is visually displayed based on the virtual fixture P.

In the bone density display operation S140, the bone density of an area in contact with the outer contour of the virtual fixture P calculated in the operation unit 132 is displayed in a different color according to the value of the bone density.

As such, in the image generation system for implant diagnosis and the method of generating an image for implant diagnosis according to the present embodiment, since the bone density around the virtual fixture P is displayed in a different color according to the value of the bone density, the user may intuitively recognize the bone density around the virtual fixture P.

Furthermore, in the method of generating an image for implant diagnosis according to the present embodiment, since the pre-matching operation is provided in which the first 3D image data is pre-matched to the second 3D image data based on the coordinate of the matching reference marker of the second 3D image data, the first 3D image data and the second 3D image data may be fast matched to each other.

As described above, according to the above-described embodiments, since the data processing apparatus for pre-matching the first 3D image data and the second 3D image data based on the plaster patterns of teeth with the matching reference marker and the coordinate of the matching reference marker of the second 3D image data is provided, the first 3D image data and the second 3D image data may be fast matched to each other.

Furthermore, according to the above-described embodiments, since the pre-matching operation for pre-matching the first 3D image data to the second 3D image data based on the coordinate of the matching reference marker of the second 3D image data is provided, the first 3D image data and the second 3D image data may be fast matched to each other.

While the inventive concept has been particularly shown and described with reference to exemplary embodiments thereof, it will be understood that various changes in form and details may be made therein without departing from the spirit and scope of the following claims.

INDUSTRIAL APPLICABILITY

The present invention relates to an image generation system for implant diagnosis and can be used in medical industry, particularly, dental industry.

The invention claimed is:

1. An image generation system for implant diagnosis comprising:
   a first image information acquirement apparatus acquiring first three-dimensional (3D) image data about a mouth area of a target patient;
   a second image information acquirement apparatus acquiring second 3D image data by scanning plaster patterns of teeth of the target patient; and
   a data processing apparatus receiving and matching the first 3D image data and the second 3D image data and generating synthetic 3D image data,
   wherein the plaster patterns of teeth are provided with a matching reference marker for matching the first 3D image data and the second 3D image data, and
   wherein the data processing apparatus generates the synthetic 3D image data by performing a pre-matching operation of pre-matching the first 3D image data and the second 3D image data based on a coordinate of a matching reference marker of the second 3D image data and then performing a precise matching operation of precisely matching the second 3D image data to the first 3D image data in the pre-matched synthetic 3D image data,
   wherein the data processing apparatus comprises:
   an input unit receiving information from a user;
   an operation unit generating the synthetic 3D image data, electrically connected to the input unit, and correcting the synthetic 3D image data based on the information input from the user; and
   a display unit electrically connected to the operation unit and visually displaying the synthetic 3D image data
   wherein, in the pre-matching operation, the operation unit sections a display area of the display unit into a teeth area display zone in which a teeth area of the target patient of the first 3D image data is visually displayed, a second 3D image data display zone in which the second 3D image data is visually displayed, and a synthetic 3D image data display zone in which the synthetic 3D image data is visually displayed,
   receives an input of the coordinate of the matching reference marker in the second 3D image data display zone through the input unit,
   receives an input of a virtual coordinate corresponding to the coordinate of the matching reference marker in the teeth area display zone through the input unit, and
   displays the pre-matched synthetic 3D image data in the synthetic 3D image data display zone by matching the input coordinate of the matching reference marker and the input virtual coordinate, wherein, in the precise matching operation, the operation unit sections the display area of the display unit into a plurality of divided zones, arranges different plane images of the pre-matched synthetic 3D image data in the plurality of divided zones, and receives an input of a state of matching the second 3D image data to the first 3D image data in each divided zone through the input unit;

wherein the plurality of divided zones comprise:

a first area in which a plane image obtained by cutting the pre-matched synthetic 3D image data along a first axis and a second axis crossing the first axis is displayed;

a second area in which a plane image obtained by cutting the pre-matched synthetic 3D image data along the second axis and a third axis crossing the second axis at a position of a first movement point displayed in the first area is displayed;

a third area in which a plane image obtained by cutting the pre-matched synthetic 3D image data along the first axis and the third axis at the position of the first movement point displayed in the first area is displayed;

a fourth area in which a plane image obtained by cutting the pre-matched synthetic 3D image data along the second axis and the third axis at a position of a second movement point displayed in the first area is displayed;

a fifth area in which a plane image obtained by cutting the pre-matched synthetic 3D image data along the first axis and the third axis at the position of the second movement point displayed in the first area is displayed; and a sixth area in which a plane image obtained by cutting the pre-matched synthetic 3D image data along the second axis and the third axis at a position of a third movement point displayed in the first area is displayed.

2. The image generation system for implant diagnosis of claim 1, wherein the matching reference marker is provided plurally, and the plurality of matching reference markers are arranged spaced apart from one another.

3. The image generation system for implant diagnosis of claim 1, wherein the first to third movement points are movable by an operation of the user, the images of the second area and the third area are changed linked with a movement of the first movement point, the images of the fourth area and the fifth area are changed linked with a movement of the second movement point, and the image of the sixth area is changed linked with a movement of the third movement point.

4. A method of generating an image for implant diagnosis, the method comprising:

a first image information acquirement operation of acquiring first 3D image data about a mouth area of a target patient;

a second image information acquirement operation of acquiring second 3D image data by scanning plaster patterns of teeth of the target patient; and a synthetic 3D image data acquirement operation of generating synthetic 3D image data by matching the first 3D image data and the second 3D image data, wherein the second image information acquirement operation comprises providing a matching reference marker for matching the first 3D image data and the second 3D image data on the plaster patterns of teeth of the target patient, and the synthetic 3D image data acquirement operation comprises a pre-matching operation of pre-matching the first 3D image data to the second 3D image data based on a coordinate of the matching reference marker of the second 3D image data and a precise matching operation of precisely matching the second 3D image data to the first 3D image data in the pre-matched synthetic 3D image data;

wherein the precise matching operation comprises:

sectioning a display area of a display unit into a plurality of divided zones and arranging different plane images of the pre-matched synthetic 3D image data in the plurality of divided zones, and performing correction such that the second 3D image data is matched to the first 3D image data in each divided area;

wherein the plurality of divided zones comprise:

a first area in which a plane image obtained by cutting the pre-matched synthetic 3D image data along a first axis and a second axis crossing the first axis is displayed;

a second area in which a plane image obtained by cutting the pre-matched synthetic 3D image data along the second axis and a third axis crossing the second axis at a position of a first movement point displayed in the first area is displayed;

a third area in which a plane image obtained by cutting the pre-matched synthetic 3D image data along the first axis and the third axis at the position of the first movement point displayed in the first area is displayed;

a fourth area in which a plane image obtained by cutting the pre-matched synthetic 3D image data along the second axis and the third axis at a position of a second movement point displayed in the first area is displayed;

a fifth area in which a plane image obtained by cutting the pre-matched synthetic 3D image data along the first axis and the third axis at the position of the second movement point displayed in the first area is displayed; and a sixth area in which a plane image obtained by cutting the pre-matched synthetic 3D image data along the second axis and the third axis at a position of a third movement point displayed in the first area is displayed.

5. The method of claim 4, wherein the pre-matching operation comprises:

sectioning a display area of a display unit into a teeth area display zone in which a teeth area of the target patient of the first 3D image data is visually displayed, a second 3D image data display zone in which the second 3D image data is visually displayed, and a synthetic 3D image data display zone in which the synthetic 3D image data is visually displayed, receiving an input of the coordinate of the matching reference marker in the second 3D image data display zone, receiving an input of a virtual coordinate corresponding to the coordinate of the matching reference marker in the teeth area display zone, and displaying the pre-matched synthetic 3D image data in the synthetic 3D image data display zone by matching the input coordinate of the matching reference marker and the input virtual coordinate.

6. The method of claim 5, wherein the matching reference marker is provided plurally, and the plurality of matching reference markers are arranged spaced apart from one another.

7. The method of claim 4, wherein the first to third movement points are movable by an operation of the user,
- the images of the second area and the third area are changed linked with a movement of the first movement point,
- the images of the fourth area and the fifth area are changed linked with a movement of the second movement point, and
- the image of the sixth area is changed linked with a movement of the third movement point.

8. The method of claim 4, wherein the second image information acquirement operation further comprises:
- generating the plaster patterns of teeth of the target patient before the providing of the matching reference marker; and
- scanning the plaster patterns of teeth of the target patient after the providing of the matching reference marker.

\* \* \* \* \*